(12) United States Patent
Wang et al.

(10) Patent No.: US 8,889,388 B2
(45) Date of Patent: Nov. 18, 2014

(54) ACOUSTIC DEVICE AND METHODS THEREOF FOR SEPARATION AND CONCENTRATION

(76) Inventors: Zhaowei Wang, Cleveland, OH (US); Donald Feke, Chesterland, OH (US); Joanne Belovich, Hinkley, OH (US)

(*) Notice: Subject to any disclaimer, the term of this patent is extended or adjusted under 35 U.S.C. 154(b) by 441 days.

(21) Appl. No.: 13/091,458

(22) Filed: Apr. 21, 2011

(65) Prior Publication Data

US 2011/0262990 A1 Oct. 27, 2011

Related U.S. Application Data

(60) Provisional application No. 61/326,330, filed on Apr. 21, 2010.

(51) Int. Cl.
| | |
|---|---|
| *C12N 13/00* | (2006.01) |
| *C12N 1/02* | (2006.01) |
| *B01D 21/28* | (2006.01) |
| *C12M 1/00* | (2006.01) |
| *B03B 5/00* | (2006.01) |

(52) U.S. Cl.
CPC ...... *C12N 1/02* (2013.01); *C12N 13/00* (2013.01); *B01D 21/283* (2013.01); *C12M 47/02* (2013.01); *B03B 5/00* (2013.01)
USPC .............. 435/173.9; 435/261; 435/308.1; 209/157; 210/513; 210/767; 210/800; 210/801; 210/802

(58) Field of Classification Search
None
See application file for complete search history.

(56) References Cited

U.S. PATENT DOCUMENTS

| | | | | |
|---|---|---|---|---|
| 3,708,263 | A  * | 1/1973 | Boucher | 422/20 |
| 2006/0037916 | A1* | 2/2006 | Trampler | 210/748 |
| 2010/0093078 | A1* | 4/2010 | Wang et al. | 435/325 |

OTHER PUBLICATIONS

Kumar, M et al. Fractionation of cell mixtures using acoustic and laminar flow fields. Biotechnology and Bioengineering. 2005. 89(2): 129-137.*

Hawkes, JJ et al. Filtration of bacteria and yeast by ultrasound-enhanced sedimentation. Journal of Applied Microbiology. 1997. 82: 39-47.*

* cited by examiner

*Primary Examiner* — Allison Fox
*Assistant Examiner* — Susan E Fernandez
(74) *Attorney, Agent, or Firm* — Fay Sharpe LLP

(57) ABSTRACT

The invention provides a settling device comprising an acoustic wave generator and an inclined settling chamber. The angle θ between the acoustic wave direction and the inclined settling chamber is greater than 0 and less than 90°. The invention also provides a concentration method and a separation method using the device. The invention can be used to concentrate or separate particles such as inorganic particles, organic particles, and biological particles, for example, mammalian cells, bacteria, yeast, algae, and plant cells. The invention exhibits technical merits such as higher efficiency, cost-effectiveness, and large-scale production.

25 Claims, 4 Drawing Sheets

ACOUSTIC DEVICE AND METHODS THEREOF FOR SEPARATION AND CONCENTRATION

INCORPORATION BY REFERENCE

This application claims the benefit of priority to U.S. Provisional Patent Application No. 61/326,330, filed Apr. 21, 2010, entitled "An Acoustic Device and Methods Thereof for Separation and Concentration", by Wang et al., the disclosure of which is incorporated herein by reference in its entirety.

BACKGROUND

The present invention relates to an acoustic device and uses thereof. It finds particular application in conjunction with separation of particles or oil droplets, and will be described with particular reference thereto. However, it is to be appreciated that the present exemplary embodiment is also amenable to other like applications.

Large-scale growth of bacteria, yeast, and mammalian cells for numerous industrial and pharmaceutical biotechnology applications use methods for cell separation. Large-scale growth of algae biomass for biodiesel production also requires separation of the cell biomass from the carrying fluid. Inclined gravity settlers have been successfully applied to cell cultures for supporting continuous perfusion culture. Devices using high frequency ultrasonic standing waves to separate particles (e.g. cells) and oil droplets from aqueous solutions have been described in Wang, Z; P. Grabenstetter, D. L. Feke, and J. Belovich. Retention and viability characteristics of mammalian cells in an acoustically driven polymer mesh, *Biotechnology Progress*, 20, 384-387, 2004; Gaida, T., Dolbhoff-Dier, O., Strutzenberger, K., Burger, W., Groschl, M., Handl, B., and Benes, E., "Selective retention of viable cells in ultrasonic resonance field devices," Biotechnol Prog., 12, 73-76, 1996; Gupta, S. and Feke, D. L. "Filtration of particulate suspensions in a acoustically driven porous media", AIChE Journal 44: 1005-1014, 1998; Kilburn, D. G., Clarke, D. J., Coakley, W. T. and Bardsley, D. W., "Enhanced sedimentation of mammalian cells following acoustic aggregation," Biotechnol. Bioeng., 34(4): 559-562, 1989; Pui, P. W. S., Trampler, F., Sonderhoff, S. A., Groeschl, M., Kilburn, D. G., and Piret, J. M., "Batch and semicontinous aggregation and sedimentation of hybridoma cells by acoustic resonance fields", Biotechnol. Prog., 11, 146, 1995; Ryll, T., Dutina, G., Reyes, A., Gunson, J., Krummen, L., Etcheverry, T. "Performance of small-scale CHO perfusion cultures using an acoustic cell filtration device for cell retention: characterization of separation efficiency and impact of perfusion on product quality", Biotechnology and Bioengineering, Vol 69, No. 4, pp. 440-449, 2000; and Trampler, F.; Piret, J. M.; Sonderhoff, S. A.; Kilburn, D. G. Acoustic filter for separating and recycling suspended particles 5626767, 1997.

However, the large scale separation of particles with diameters 1-20 microns from aqueous solution is difficult to accomplish in a cost-effective manner. Advantageously, the present invention provides an improved settling device and uses thereof that overcome these problems.

BRIEF DESCRIPTION

One embodiment provides a device including (i) an acoustic wave generator; (ii) an inclined settling chamber; (iii) an inlet for introducing a material into said inclined settling chamber; and (iv) at least two outlets for said material to exit from said settling chamber. The acoustic wave from the acoustic wave generator passes through at least a portion of the inclined settling chamber. The angle $\theta$ between the acoustic wave direction and the inclined settling chamber is greater than 0 and less than 90°.

Another embodiment of the invention provides a method of concentrating an entity in a flow medium by (i) introducing the entity in the flow medium into the inclined settling chamber via the inlet; (ii) flowing the entity in the flow medium inside the inclined settling chamber; (iii) passing an acoustic wave through at least a portion of the inclined settling chamber; and (iv) collecting the entity in the flow medium from the at least two outlets. The entity portion collected from one outlet has a concentration in the flow medium which is different from that of the entity portion collected from another outlet.

Still another embodiment provides a method of separating at least two entities in a flow medium by (i) introducing the at least two entities in the flow medium into the inclined settling chamber via the inlet; (ii) flowing the at least two entities in the flow medium inside the inclined settling chamber; (iii) passing an acoustic wave through at least a portion of the inclined settling chamber; and (iv) collecting the at least two entities in the flow medium from the at least two outlets. Each entity as collected from one outlet has a concentration in the flow medium which is different from that of the same entity collected from another outlet.

DETAILED DESCRIPTION

Figure 1:
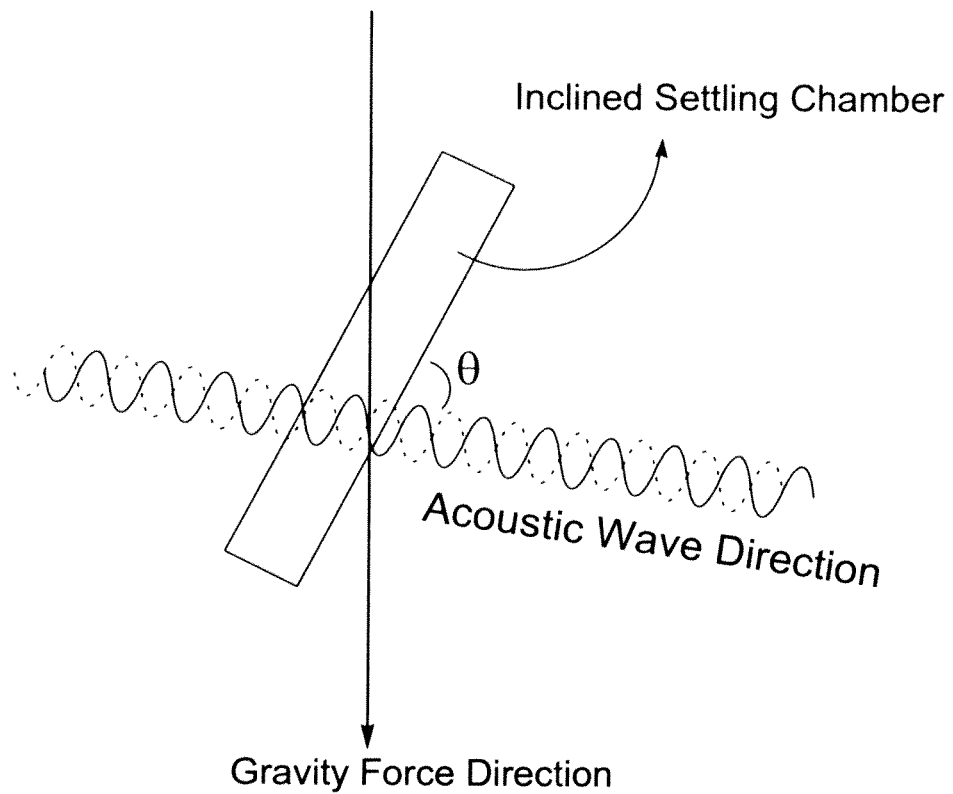
FIG. 1 illustrates the angle $\theta$ between the acoustic wave direction and the inclined settling chamber in an embodiment of the invention.

As shown in FIG. 1, the angle $\theta$ between the acoustic wave direction and the inclined settling chamber should be understood as the acute angle, one of the two angles as formed between any two straight lines that are neither perpendicular nor parallel to each other. If the acute angle is not required, the angle $\theta$ would be from greater than 0 and less than 90° and greater than 90° and less than 180°. In a preferred embodiment, the acute angle $\theta$ is from 30° to 89° such as 80° to 85°, for example, 83.2°.

There is no specific limitation on the angle between the inclined settling chamber and the gravity. For example, the angle may be from 0 to 90°, preferably from 0.1° to 89.9°.

The acoustic wave may be, for example, a standing acoustic wave, which can be generated by means of a piezoelectric transducer, a reflector, and a medium such as a fluid medium (e.g. water) in which the wave propagates. The acoustic wave may have a frequency in the range of from about 0.1 MHz to about 10 MHz, preferably from 1.5 MHz to 2.5MHz, such as 2.1 MHz. The rate of energy dissipation in the medium such as a fluid medium may be greater than 0 Watt/Liter and less than 1 Kilowatt/Liter, preferably less than 0.2 Kilowatt/Liter.

The acoustic wave may pass through at least 30%, preferably at least 50%, and more preferably at least 80%, of the volume of the inclined settling chamber.

The device of the present invention may further comprise a temperature controller for the inclined settling chamber. In an embodiment, the temperature controller comprises a cooling chamber using a liquid such as water as a coolant, which also acts as a transferring medium to make sure the acoustic wave travels in the inclined settling chamber in the direction upright to the acoustic wave generator such as a transducer. In a preferred embodiment, the acoustic wave from said acoustic wave generator passes through the coolant before it passes through at least a portion of the inclined settling chamber.

In various embodiments, the invention provides an ultrasonic separator with oblique settling chambers, which combines the features of both a gravity settler and an ultrasonic system to efficiently recover particles, cells, or oil droplets from an aqueous stream. The ultrasonic separator may be composed of three chambers, in which the walls of the middle chamber are at an oblique incline with the acoustic transducers. Particles or oil droplets in the fluid can be separated from the fluid under the combined effects of acoustic, gravity and hydraulic drag forces. This design leads to greater efficiency of particle recovery compared to previous designs in which the separation chamber is parallel to the transducers.

There is no specific limitation on the position of the at least two outlets. For example, they may generally locate at the same end, such as the lower end, of the inclined settling chamber. However, for oil droplet separation, the inlet for an emulsion may locate at the low end and the at least two outlets may locate on the upper end. The oil droplets may aggregate and form large drops and then float. Finally they reach the upper surface of the inclined settling chamber and then flow along the upper surface and leave the chamber via one outlet in the upper end while the relatively clarified stream leaves the chamber via another outlet.

The method of concentrating an entity in a flow medium using the device of the invention may further comprise a step of controlling the temperature inside the inclined settling chamber within a pre-determined range, for example, by controlling the temperature outside the inclined settling chamber such as a coolant (e.g. water). The entity subject to the concentration may comprise particles having a size in the range of from about 0.1 micron to about 50 microns. The particles may be selected from inorganic particles, organic particles, biological particles, and any combination thereof. Examples of biological particles may include single-celled organisms, such as mammalian cells, bacteria, yeast, algae, plant cells, and any combination thereof. In an embodiment, the single-celled organisms comprise cells cultured in suspension mode such as hybridoma cells, CHO cells, and any combination thereof. These particles generally have a density greater than the flow medium (the host fluid), and as such, the inlet will be placed higher than the at least two outlets. If the particles have a density lower than the flow medium (the host fluid), the inlet will be placed lower than the at least two outlets, similar to the embodiment as described above for oil droplet separation. However, it should be understood that density is not the only factor in the design of the device, and other factors such the hydraulic drag force of the liquid medium as well as the acoustic wave should also be considered. For example, an up-flowing medium may carry the particles upward with the aid of hydraulic drag force, despite that the particles may have a density greater than, but not significantly greater than, the flow medium (the host fluid). Under the circumstance, the inlet will not have to be placed higher than the at least two outlets, and it may be placed lower than the at least two outlets. It should also be understood that, because of the multiple factors, the invention may be used to separate or concentrate particles with same diameter and same density but different acoustic contrast factor.

In the concentration method, the flow medium may be an aqueous medium, the flow rate of which in the inclined settling chamber may be in the range of from about 16 L/day to about 34 L/day.

Similar to the concentration method, the method of separating at least two entities in a flow medium such as an aqueous medium using the device of the invention may further comprise a step of controlling the temperature inside the inclined settling chamber within a pre-determined range. The at least two entities may comprise particles having a size in the range of from about 0.1 micron to about 50 microns, for example, inorganic particles, organic particles, biological particles, and any combination thereof. The biological particles may comprise single-celled organisms selected from mammalian cells, bacteria, yeast, algae, plant cells, and any combination thereof. In an embodiment, the single-celled organisms comprise cells cultured in suspension mode such as hybridoma cells, CHO cells, and any combination thereof.

Figure 2:
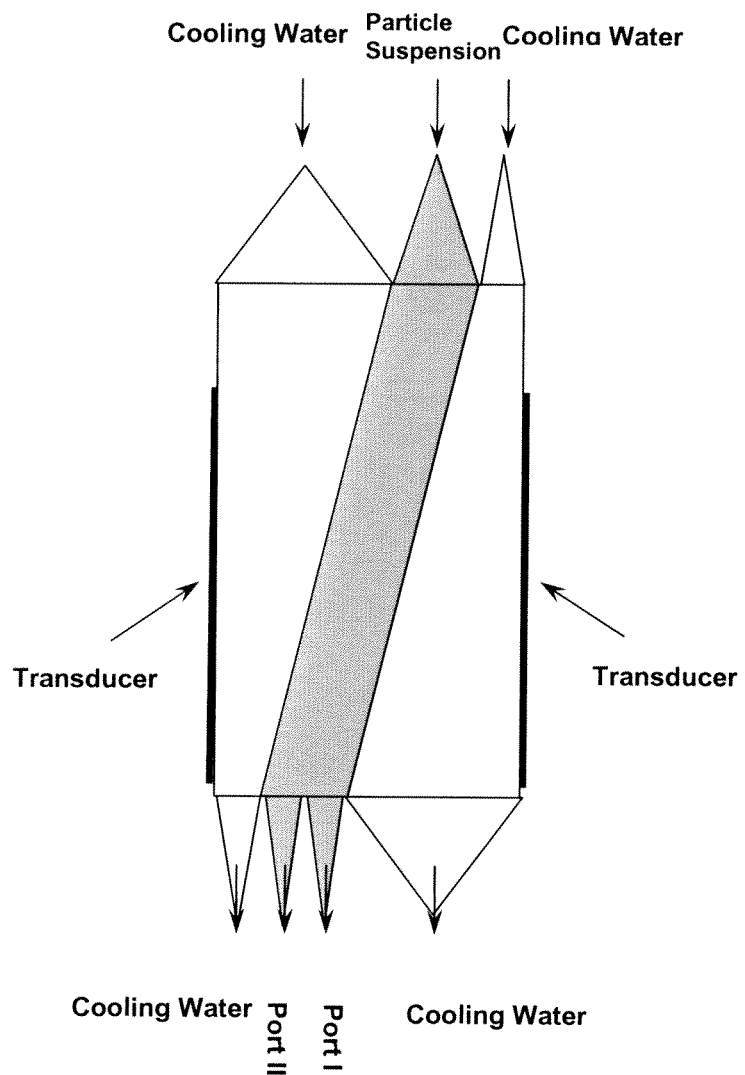
FIG. 2 schematically illustrates an ultrasonic separator for solid particle separation in an embodiment of the invention.

In an embodiment, the invention utilizes high frequency ultrasonic standing waves to retain and separate solid particles in an ultrasonic separator, as shown in FIG. 2. With reference to FIG. 2, an ultrasonic separator consists of three chambers. The middle or central chamber is the inclined settling chamber, which is the functioning part of the device, with walls that are at oblique angles with the transducers. There may be transducers on both sides of the device. Alternatively, the device may contain only one transducer on one side, and a reflecting material on the other side. There are two outlet ports at one end of the middle chamber, one of which is for concentrated particles and the other is for clarified fluid. Water is pumped through the two side chambers (cooling chambers) to prevent the heat accumulation generated by the acoustic transducers. The particle suspension may enter the central chamber from the top inlet, or alternatively a lower inlet (not shown in the figure), and the suspended particles are driven to the nodal planes by ultrasonic forces. For the embodiment with the top inlet as shown in FIG. 2, when the amount of particles accumulated at the nodal planes reaches a critical level, the force due to gravity overwhelms the acoustic force and the particles move downward until they reach the inclined plane, a thin film, which separates the functioning chamber from the cooling chambers. The particles on the film slide down along the film and exit the chamber via an exit (port I), while the clarified fluid is pumped out via another exit (port II). In this embodiment, the device is used to separate particles from the fluid, or concentrate the particles. In the embodiment where the inlet locates lower than the at least two outlets, such as for particles or oil droplets with lower density than the host fluid, the droplets will accumulate at the antinodal planes, and the collected droplets and fluid will leave the chamber from the upper end of the device.

Figure 3:
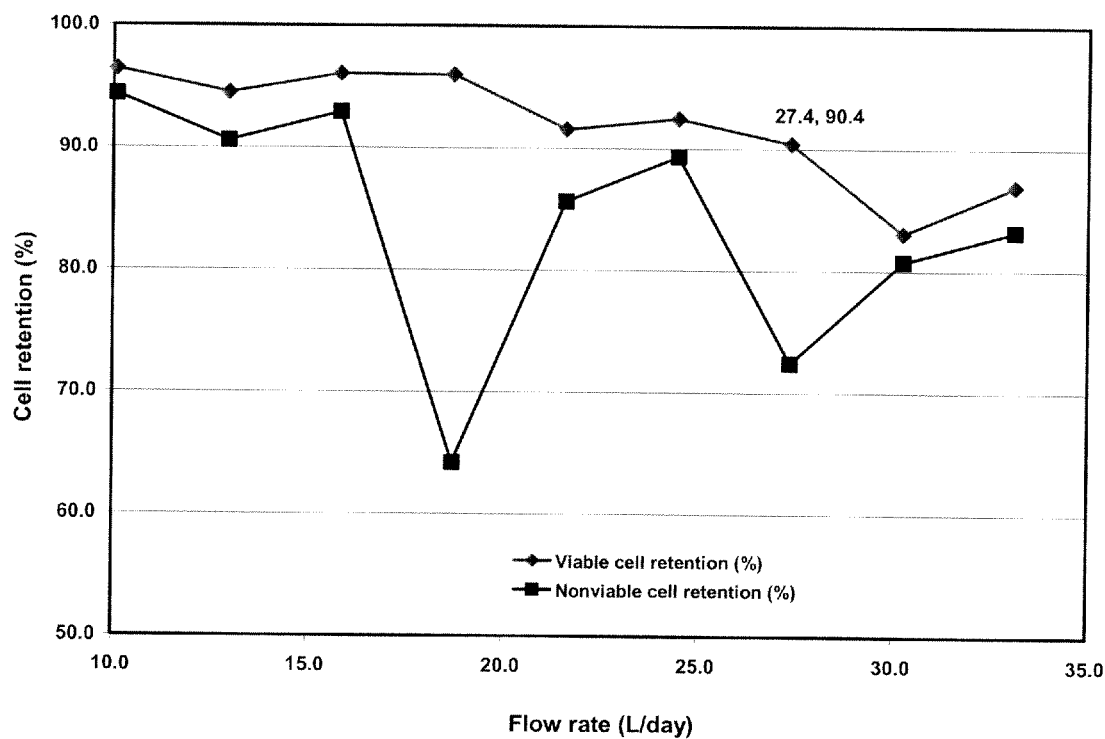
FIG. 3 shows the cell retention vs. flow rate of HB-159 hybridoma cells in an embodiment of the invention.

The trajectory of the particle depends on the balance of the hydraulic, acoustic, and gravity forces. The hydraulic force is proportional to the flow rate and to the particle radius, while the acoustic force experienced by a particle is proportional to the cube of the particle's radius. Thus, the small particles move along with fluid and leave the middle chamber via port II while the larger particles move to the nodal plane, and eventually settle onto the inclined lower surface and exit via port I. In this way, the manipulation of the flow rate and the strength of the ultrasonic field are used to separate particles based on their size. FIG. 3 shows the cell retention vs. flow rate with signal generator voltage of 2.8V and average power input on the transducers of 13.9 W. The cell line used was HB-159 hybridoma. As shown in FIG. 3, viable cell retention was always higher than that of nonviable cells. This consistent difference implies that the nonviable cells can be preferentially removed while most of the viable cells can be retained in the perfusion culture system. If the middle chamber is viewed as an inclined gravity settler, this device has a cell retention capacity that is about 22 times that of an inclined gravity settler with the same surface area but without the ultrasonic enhancement.

Figure 4:
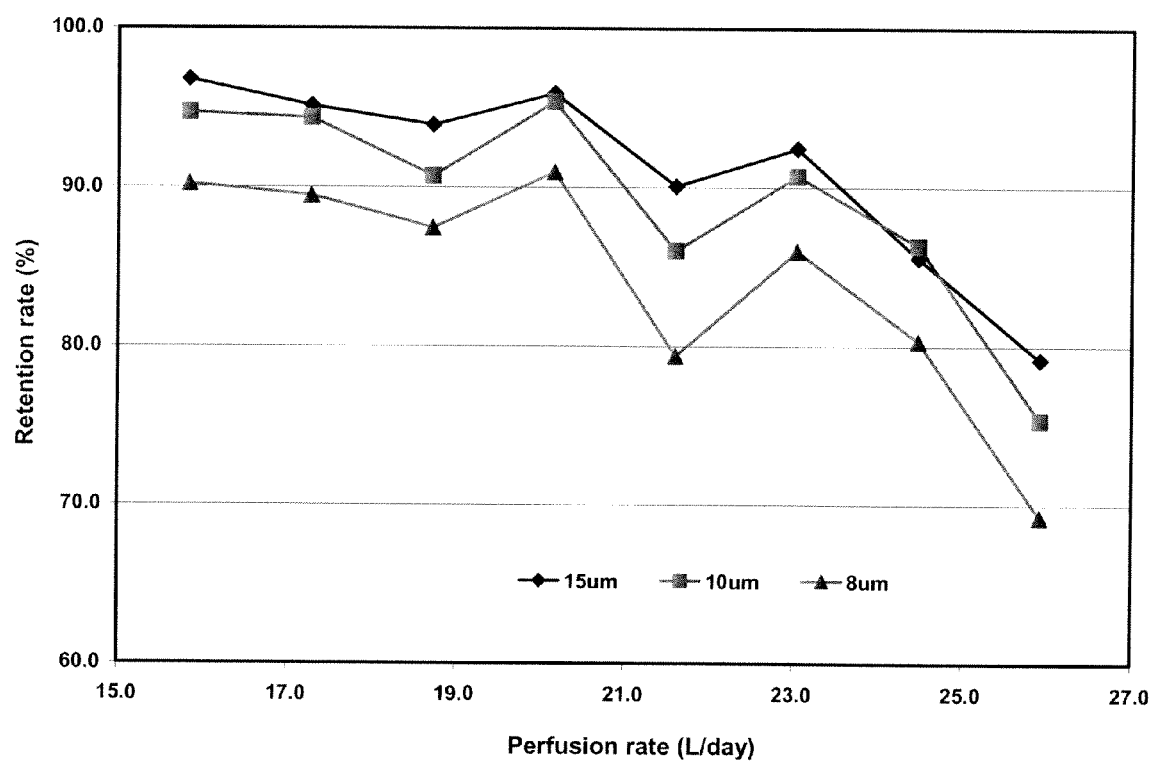
FIG. 4 shows the particle retention vs. perfusion rate for particle suspension consisting of 8 µm, 10 µm and 15 µm polystyrene particles in an embodiment of the invention.

FIG. 4 shows the particle retention vs. perfusion rate for particle suspension consisting of 8 μm, 10 μm and 15 μm polystyrene particles. Voltage input at the signal generator is 900 mVpp and average power input at the transducer is 1 W. As shown in FIG. 4, the particle retention capacity of the device is confirmed and the retention rate drops along with the decrease of the diameter of the polystyrene particle. This result confirms the finding shown in FIG. 3, that the system can fractionate the particles according to size.

The exemplary embodiments have been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A device comprising:
   (i) an acoustic wave generator;
   (ii) an inclined settling chamber including first and second side walls and first and second end walls;
   (iii) an inlet on the first end wall for introducing a material into said inclined settling chamber; and
   (iv) at least two outlets on the second end wall for said material to exit said inclined settling chamber;
   wherein the acoustic wave from the acoustic wave generator passes through at least a portion of the inclined settling chamber along an acoustic wave direction; and
   wherein the angle θ between the acoustic wave direction and either the first or second side wall of the inclined settling chamber is greater than 0° and less than 85°.

2. The device according to claim 1, wherein the second end wall is a lower end of said inclined settling chamber.

3. The device according to claim 1, wherein the acoustic wave generator is an acoustic transducer.

4. The device according to claim 1, wherein the acoustic wave is a standing acoustic wave.

5. The device according to claim 1, wherein the acoustic wave has a frequency in the range of from about 0.1 MHz to about 10 MHz.

6. The device according to claim 1, wherein the angle θ is from 80° to 85°.

7. The device according to claim 1, wherein the energy dissipation from the acoustic wave is greater than 0 Watt/Liter and less than 1 Kilowatt/Liter.

8. The device according to claim 1, wherein the acoustic wave passes through at least 30% volume of the inclined settling chamber.

9. The device according to claim 1, further comprising a temperature controller for the inclined settling chamber.

10. The device according to claim 9, wherein the temperature controller comprises a cooling chamber using a liquid as a coolant, the coolant acting as a transferring medium to keep the acoustic wave traveling in the inclined settling chamber along the acoustic wave direction.

11. The device according to claim 10, wherein the acoustic wave from said acoustic wave generator passes through the coolant before it passes through at least a portion of the inclined settling chamber.

12. The device according to claim 10, wherein the acoustic wave generator is disposed on the cooling chamber and the inclined settling chamber is adjacent the cooling chamber.

13. A method of concentrating an entity in a flow medium comprising:
   (i) introducing the entity in the flow medium into an inclined settling chamber;
   (ii) flowing the entity in the flow medium inside the inclined settling chamber;
   (iii) passing an acoustic wave through at least a portion of the inclined settling chamber and along an acoustic wave direction that intersects a sidewall of the inclined settling chamber, wherein the angle θ between the acoustic wave direction and either the first or second side wall of the inclined settling chamber is greater than 0° and less than 85°; and
   (iv) collecting the entity in the flow medium from at least two outlets; wherein the entity portion collected from one outlet has a concentration in the flow medium which is different from that of the entity portion collected from second outlet.

14. The method according to claim 13, further comprising controlling the temperature inside the inclined settling chamber within a pre-determined range.

15. The method according to claim 13, wherein the entity comprises particles selected from inorganic particles, organic particles, biological particles, and any combination thereof.

16. The method according to claim 15, wherein the biological particles are selected from mammalian cells, bacteria, yeast, algae, plant cells, and any combination thereof.

17. A method of separating at least two entities in a flow medium comprising:
   (i) introducing the at least two entities in the flow medium into an inclined settling chamber;
   (ii) flowing the at least two entities in the flow medium inside the inclined settling chamber;
   (iii) passing an acoustic wave through at least a portion of the flow medium inside the inclined settling chamber and along an acoustic wave direction that intersects a sidewall of the inclined settling chamber, wherein the angle θ between the acoustic wave direction and either the first or second side wall of the inclined settling chamber is greater than 0° and less than 85°; and
   (iv) collecting the at least two entities in the flow medium from at least two outlets; wherein each entity of the at least two entities as collected from one outlet has a concentration in the flow medium which is different from that of the same entity collected from a second outlet.

18. The method according to claim 17, further comprising controlling the temperature inside the inclined settling chamber within a pre-determined range.

19. The method according to claim 17, wherein the at least two entities are selected from mammalian cells, bacteria, yeast, algae, plant cells, and any combination thereof.

20. The method according to claim 17, wherein the at least two entities comprise a first entity including nonviable cells, and a second entity including viable cells.

21. The method according to claim 17, wherein the at least two entities comprise a first entity and a second entity; the second entity has a bigger size than the first entity; and the second entity has a higher settling speed under the influence of the acoustic wave.

22. A device comprising:
(i) at least one cooling chamber including a coolant;
(ii) an acoustic wave generator disposed on the at least one cooling chamber;
(iiii) an inclined settling chamber adjacent the at least one cooling chamber and including first and second side walls and first and second end walls;
(iv) an inlet on the first end wall for introducing a material into said inclined settling chamber; and
(v) at least two outlets on the second end wall for said material to exit said inclined settling chamber;
wherein the acoustic wave from the acoustic wave generator passes through the coolant and at least a portion of the inclined settling chamber along an acoustic wave direction; and
wherein the angle θ between the acoustic wave direction and the first and second side walls of the inclined settling chamber is greater than 0° and less than 85°.

23. The device according to claim 22, further including first and second cooling chambers adjacent the inclined setting chamber, wherein the first cooling chamber is adjacent the first side wall and the second cooling chamber is adjacent the second side wall.

24. The device according to claim 23, further including a second acoustic wave generator disposed on the second side wall.

25. The device according to claim 22, wherein the angle θ between the acoustic wave direction and either the first or second side wall of the inclined settling chamber is from 80° to 85°.

* * * * *